US010772949B2

(12) United States Patent
Lai et al.

(10) Patent No.: US 10,772,949 B2
(45) Date of Patent: Sep. 15, 2020

(54) DENGUE VIRUS GLYCOPROTEIN E DIII VARIANTS AND USES THEREOF

(71) Applicant: ALBERT EINSTEIN COLLEGE OF MEDICINE, Bronx, NY (US)

(72) Inventors: Jonathan R. Lai, Dobbs Ferry, NY (US); Margaret C. Kielian, Dobbs Ferry, NY (US); Julia C. Frei, Bronx, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 0 days.

(21) Appl. No.: 16/064,505

(22) PCT Filed: Feb. 13, 2017

(86) PCT No.: PCT/US2017/017637

§ 371 (c)(1),
(2) Date: Jun. 21, 2018

(87) PCT Pub. No.: WO2017/142831

PCT Pub. Date: Aug. 24, 2017

(65) Prior Publication Data

US 2018/0360946 A1 Dec. 20, 2018

Related U.S. Application Data

(60) Provisional application No. 62/295,634, filed on Feb. 16, 2016.

(51) Int. Cl.

| | |
|---|---|
| ***A61K 39/12*** | (2006.01) |
| ***C07K 14/005*** | (2006.01) |
| ***A61P 31/14*** | (2006.01) |
| ***C12N 7/00*** | (2006.01) |
| *A61K 39/00* | (2006.01) |

(52) U.S. Cl.
CPC .............. *A61K 39/12* (2013.01); *A61P 31/14* (2018.01); *C07K 14/005* (2013.01); *C12N 7/00* (2013.01); *A61K 2039/55566* (2013.01); *C12N 2770/24122* (2013.01); *C12N 2770/24134* (2013.01); *Y02A 50/386* (2018.01)

(58) Field of Classification Search
CPC .................. A61K 39/12; C07K 14/005; C12N 2770/24122; C12N 2770/24134
See application file for complete search history.

(56) References Cited

U.S. PATENT DOCUMENTS

2010/0291144 A1 11/2010 Ramanathan et al.

FOREIGN PATENT DOCUMENTS

| | | | |
|---|---|---|---|
| CN | 102199617 | A | 9/2011 |
| WO | 2013059493 | A1 | 4/2013 |
| WO | 2016012800 | A1 | 1/2016 |

OTHER PUBLICATIONS

Chokephaibulkit, K., and G. C. Perng, 2013, Challenges for the formulation of a universal vaccine against dengue, Exp. Biol. Med. 238:566-578.*

Jin, X., et al., 2009, Dengue vaccine development and dengue viral neutralization and enhancement assays, Antivirl Ther. 14:739-749.*

Murphy, B. R., and S. S. Whitehead, 2011, Immune response to dengue virus and prospects for a vaccine, Ann. Rev. Immunol. 25:587-619.*

Thomas, S. J., and A. L. Rothman, 2015, Trials and tribulations on the path to developing a dengue vaccine, Am. J. Prev. Med. 49(6S4):S334-S344.*

PCT International Search Report and Written Opinion dated May 26, 2017 for PCT International Patent Application No. PCT/US2017/017637, 9 pages.

Frei et al., "Comprehensive mapping of functional epitopes on dengue virus glycoprotein E DIII for binding to broadly neutralizing antibodies 4E11 and 4E5A by phage display," Virology, Sep. 2, 2015, vol. 485, pp. 371-382.

Brien et al., "Genotype-Specific Neutralization and Protection by Antibodies against Dengue Virus Type 3," Journal of Virology, Aug. 11, 2010, vol. 84, No. 20, pp. 10630-10643.

* cited by examiner

*Primary Examiner* — Jeffrey S Parkin
(74) *Attorney, Agent, or Firm* — Foley Hoag LLP

(57) ABSTRACT

Specific Dengue virus glycoprotein subunit E DIII variants and their uses in preventing and treating Dengue virus infection are disclosed.

21 Claims, 7 Drawing Sheets

Specification includes a Sequence Listing.

DENGUE VIRUS GLYCOPROTEIN E DIII VARIANTS AND USES THEREOF

CROSS-REFERENCE TO RELATED APPLICATIONS

This application is a U.S. national stage entry under 35 U.S.C. § 371 of PCT International Patent Application No. PCT/US2017/017637, filed Feb. 13, 2017, which claims the benefit of U.S. Provisional Patent Application No. 62/295,634, filed Feb. 16, 2016, the contents of each of which are incorporated herein by reference into the subject application.

STATEMENT OF GOVERNMENT SUPPORT

This invention was made with government support under grant numbers AI090249 and AI128090 awarded by the National Institutes of Health. The government has certain rights in the invention.

BACKGROUND OF THE INVENTION

Throughout this application various publications are referred to in parentheses. Full citations for these references may be found at the end of the specification. The disclosures of these publications are hereby incorporated by reference in their entirety into the subject application to more fully describe the art to which the subject invention pertains.

Dengue virus is the leading arthropod-transmitted viral disease in the world with approximately 390 million human infections per year (1). Nearly 3.6 billion people live in at risk areas for infection, and the global distribution of the two mosquito species that carry the virus (*Aedes aegypti* and *Aedes albopictus*) is expanding beyond tropical regions and reaches as far north as New York in North America (2). Primary infection by one of the four Dengue virus serotypes (DENV1-4) typically causes a significant but self-limiting febrile illness, whereas secondary infections can lead to severe disease characterized by hemorrhagic fever and shock syndrome (Severe Dengue or Dengue Hemorrhagic Fever (DHF) or Dengue Shock Syndrome (DSS)). These latter syndromes occur in a minor fraction (1% or less) of secondary infections but lead to hospitalization and, in some cases, death. DHF and DSS are thought to arise from a process known as antibody-dependent enhancement (ADE) of infection. In an increasingly accepted model, ADE is caused by antibodies elicited during the course of primary infection that may be potently neutralizing against the primary infection serotype, but also have some cross-reactivity or weak neutralization potential against other serotypes (3). During secondary infection by a heterologous DENV serotype, these antibodies promote uptake and infection of the un-neutralized virus in Fc-γ receptor (FcγR) expressing cells, ultimately increasing viremia. This leads to greater levels of pro-inflammatory cytokines (e.g., IL-1β, TNF-α, IL-6, IFN-γ) and the viral NS1 protein in serum, both of which compromise junctional integrity of capillary endothelial cells (3). Structural proteins encoded by the DENV genome diverge by as much as 40% in amino acid sequence among the four serotypes, and within each of the serotypes, individual genotypes vary by ~3%. Thus a critical objective for Dengue virus vaccine design is to elicit a broadly neutralizing antibody response against all four serotypes, since weakly cross-reactive antibodies may actually increase the risk of ADE.

Three Dengue vaccine candidates are in clinical development, all of which consist of tetravalent mixtures of attenuated or chimeric viruses. In recently published phase III trials, Sanofi's Dengvaxia®, a tetravalent mixture of yellow-fever virus vector containing DENV1-4 glycoprotein, provided only partial efficacy (<70%) in seropositive cases, and was not effective at all for naïve individuals (4). Nonetheless, Dengvaxia® was recently approved for use in Mexico, the Philippines, Brazil and several other countries in children over the age of 9 who are presumably already flavivirus immune. Two other candidate vaccines are in moving into phase III trials (DENVax, Takeda; and TV003/TV005, NIAID); yet, both also elicited incomplete levels of neutralizing antibody responses (5, 6). Therefore, there is significant rationale for development of alternative vaccine platforms for use either as next-generation primary vaccines, or as boosting agents to improve the efficacy of existing live virus vaccines.

The mature, prefusion glycoprotein E exists as a head-to-tail dimer organized into rafts with icosahedral geometry on the viral particle (7, 8). Each E subunit contains three domains, DI, DII, and DIII. DII contains the fusion loop that inserts into the host cell upon initiation of the fusion reaction in the endosome; DI acts as a rigid connector to DIII, which is anchored via the stem and C-terminal TM domain into the viral membrane. The post-fusion E structure is a trimer with the DIII domain and stem region significantly relocated relative to DI and DII, so as to bring the host and viral membranes into proximity to facilitate viral membrane fusion (9). A host receptor has yet to be identified, but there is circumstantial evidence that interactions between cellular components and DIII initiate attachment and infection (10-12). Neutralizing antibodies arising during infection target a variety of epitopes on the E glycoprotein. Potent and cross-neutralizing antibodies appear to be directed toward either complex quaternary epitopes whose constituents involve portions of the E domains on adjacent dimer subunits (13, 14), or toward the lateral ridge on DIII formed by the A and G strands (15, 16). One example of a DIII-specific broadly neutralizing antibody (bNAb) is the murine mAb 4E11 that potently neutralizes DENV1-3 and weakly neutralizes DENV4 (see ref. (15) for the crystal structure of the DIII-4E11 complex). Recently, high-throughput mutagenesis ("combinatorial alanine scanning") was used to quantify energetic contributions of contact residues on DIII from all four serotypes recognition feature for 4E11 (17).

Immunization of mice and non-human primates with recombinant DIII constructs (EDIIIs) leads to strong antibody responses, but these antibodies are poorly neutralizing or limited in breadth (18-28). In mice, the immunodominant regions of DIII appear to be in the AB- and FG-loops; resulting monoclonal antibodies are either cross-reactive and non-neutralizing (AB-loop) or type-specific and variably neutralizing (FG-loop) (26, 27). Antibodies that target other domains or more complex epitopes predominate in the human response during the course of natural infection (13, 14, 29, 30). Immunization of non-human primates with EDIII generates a high DIII-specific antibody titer (19, 23, 28). Other immunogen strategies that focus on more complex epitopes or on mimicking the prefusion E dimer are being explored (31), but EDIII has the advantage of being relatively small and easy to produce in large quantities. Dengue EDIII has high potential as an immunogen target, but previous attempts to improve its qualities have not been successful. One strategy to decrease the complexity of tetravalent cocktails is to produce EDIII fusion proteins linking EDIIIs from the four serotypes by flexible linkers ("beads on a string"), but this approach resulted in an imbalanced neutralizing titer response in mice and only partial protection in a suckling mice model for DENV1, 2, and 4 (25). Another strategy is engineering of a "consensus" DIII, in which conserved segments were emphasized (23). However, this approach led to DENV2-specific responses in non-human primates.

The present invention addresses the need for improved methods for preventing and treating Dengue virus infections by providing protein immunogens based on the Dengue virus glycoprotein subunit E domain III (EDIII).

SUMMARY OF THE INVENTION

Provided are specific Dengue virus glycoprotein subunit E DIII variants and their uses in preventing and treating Dengue virus infection.

DETAILED DESCRIPTION OF THE INVENTION

Figure 1A:
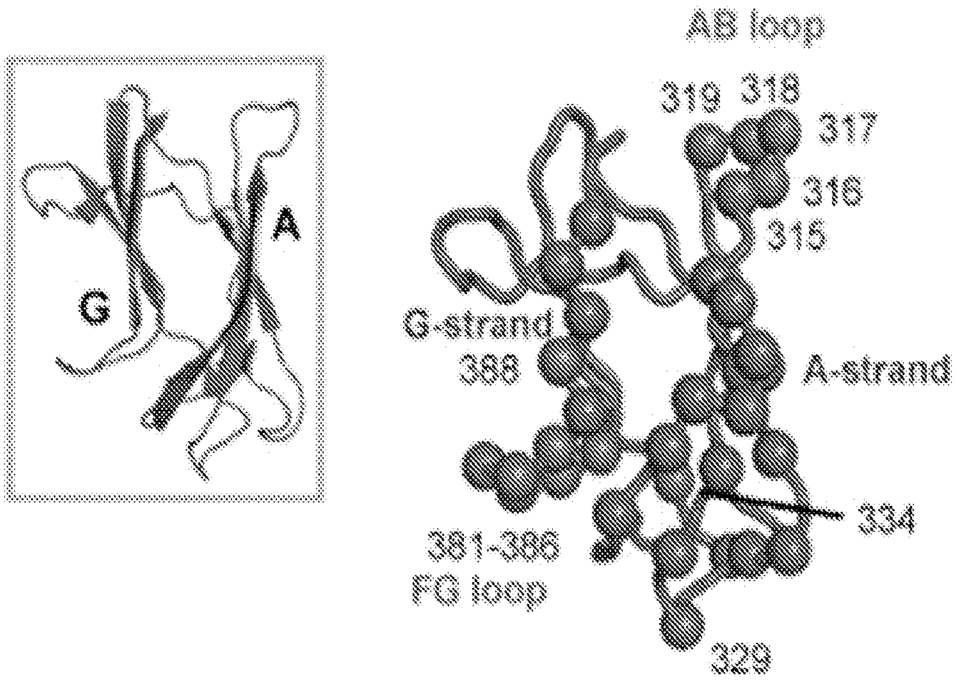
FIG. 1A-1C. Design of the resurfacing libraries. View down the A/G strand of DENV2 EDIII (inset shows orientation). Some sphere indicate 4E11 contact residues, other spheres indicate positions that were randomized, focusing on the AB- and FG-loops. (B) Phage ELISA of the rsDIIIs for binding to 4E11, all comparable to DENV2 EDIII WT. (C) High point phage ELISA reactivity profiles of rsDIIIs for 4E11 (A/G strand epitope), 2H12 (AB-loop epitope), 3H5-1 (FG-loop epitope), M2 (expression control) and 1% BSA (negative control).

The present invention provides a Dengue virus glycoprotein subunit E DIII variant comprising variant Ser27 (SEQ ID NO:1), variant SerD1 (SEQ ID NO:2), variant Ala1 (SEQ ID NO:3), variant Ala2 (SEQ ID NO:4), variant Ala3 (SEQ ID NO:5), variant Ala5 (SEQ ID NO:6), variant Ala11 (SEQ ID NO:7), or variant Ala30 (SEQ ID NO:8).

In one embodiment, the variant consists of the specified variant. In one embodiment, the variant consists essentially of the specified variant, wherein any elements added to the specified variant do not decrease the immunogenic properties of the specified variant.

The engineered Dengue virus glycoprotein subunit E DIII variants have the amino acid sequences set forth below. The underlined portions of the sequences below correspond to the amino acid residues set forth for the corresponding sequences in Table 1.

```
Ser27 (SEQ ID NO: 1):
DYKDDDDKGSGMSYSMCTGKFKIVKEIASTSHGTIVIRVQYEGDGSPCK

IPFEIMDLEKRHVLGRLITVNPIVTEKDSPVNIEAEPPFGDSYIIIGVE

SSQLSLNWFKKGSSIGQHHHHHHHH

SerD1 (SEQ ID NO: 2):
DYKDDDDKGSGMSYSMCTGKFKIVKEIAESSSGTIVIRVQYEGYGSPCK

IPFEIMDLEKRHVLGRLITVNPIVTEKDSPVNIEAEPPFGDSYIIIGVE

SAQLKLNWFKKGSSIGQHHHHHHHH

Ala1 (SEQ ID NO: 3):
DYKDDDDKGSGMSYSMCTGKFKIVKEIAAAAAGTIVIRVQYEGDGSPCK

IPFEIMDLEKRHVLGRLITVNPIVTEKDSPVNIEAEPPFGDSYIIIGVA

PGQLELNWFKKGSSIGQHHHHHHHH

Ala2 (SEQ ID NO: 4):
DYKDDDDKGSGMSYSMCTGKFKIVKEIAAAAADATIVIRVQYEGDGSPCE

IPFEIMDLEKRHVLGRLITVNPIVTEKDSPVNIEAEPPFGDSYIIIGVE

AAELKLNWFKKGSSIGQHHHHHHHH

Ala3 (SEQ ID NO: 5):
DYKDDDDKGSGMSYSMCTGKFKIVKEIAAAQAGTIVIRVQYEGDGSPCK

IPFEIMDLEKRHVLGRLITVNPIVTEKDSPVNIEAEPPFGDSYIIIGAA

AGALELNWFKKGSSIGQHHHHHHHH

Ala5 (SEQ ID NO: 6):
DYKDDDDKGSGMSYSMCTGKFKIVKEIAATADATIVIRVQYEGDGSPCK

IPFEIMDLEKRHVLGRLITVNPIVTEKDSPVNIEAEPPFGDSYIIIGAE

AAPLTLNWFKKGSSIGQHHHHHHHH

Ala11 (SEQ ID NO: 7):
DYKDDDDKGSGMSYSMCTGKFKIVKEIAEAAPGTIVIRVQYEGDGSPCK

IPFEIMDLEKRHVLGRLITVNPIVTEKDSPVNIEAEPPFGDSYIIIGAE

PGELTLNWFKKGSSIGQHHHHHHHH

Ala30 (SEQ ID NO: 8):
DYKDDDDKGSGMSYSMCTGKFKIVKEIAETQDGTIVIRVQYEGDGSPCK

IPFEIMDLEKRHVLGRLITVNPIVTEKDSPVNIEAEPPFGDSYIIIGAE

PAALELNWFKKGSSIGQHHHHHHHH.
```

The amino acids are encoded by the following DNA sequences:

```
Ser27 (SEQ ID NO: 9):
gactacaaggatgatgacgacaaaggcagcggcatgagctatagcatgtgcaccggcaaatttaaaatcgtgaa

agagatcgcctcgacgtcgcacggtaccattgtgatccgtgtgcagtatgaaggcgatggtagcccgtgcaaaa

tcccgttcgagatcatggacctggagaaacgccatgtgctgggtcgcctgattaccgtgaacccgattgtgacc
```

-continued gagaaagatagcccggtgaacattgaagccgaaccgccgttcggcgatagctacattatcattggtgttgagtc tagtcagctgagcctgaactggttcaagaagggcagcagcattggccagcatcatcatcatcatcatcatcatt aa SerD1 (SEQ ID NO: 10):
gactacaaggatgatgacgacaaaggcagcggcatgagctatagcatgtgcaccggcaaatttaaaatcgtgaa agagatcgccgagtcgtcgagcggtaccattgtgatccgtgtgcagtatgaaggctacggtagcccgtgcaaaa tcccgttcgagatcatggacctggagaaacgccatgtgctgggtcgcctgattaccgtgaacccgattgtgacc gagaaagatagcccggtgaacattgaagccgaaccgccgttcggcgatagctacattatcattggtgttgagtc tgctcagctgaaactgaactggttcaagaagggcagcagcattggccagcatcatcatcatcatcatcatcatt aa Ala1 (SEQ ID NO: 11):
gactacaaggatgatgacgacaaaggcagcggcatgagctatagcatgtgcaccggcaaatttaaaatcgtgaa agagatcgccgcagctgcagctggtaccattgtgatccgtgtgcagtatgaaggcgatggtagcccgtgcaaaa tcccgttcgagatcatggacctggagaaacgccatgtgctgggtcgcctgattaccgtgaacccgattgtgacc gagaaagatagcccggtgaacattgaagccgaaccgccgttcggcgatagctacattatcattggtgttgcacc aggtcaactggaactgaactggttcaagaagggcagcagcattggccagcatcatcatcatcatcatcatcatt aa Ala2 (SEQ ID NO: 12):
gactacaaggatgatgacgacaaaggcagcggcatgagctatagcatgtgcaccggcaaatttaaaatcgtgaa agagatcgccgcagctgcagatgctaccattgtgatccgtgtgcagtatgaaggcgatggtagcccgtgcgaaa tcccgttcgagatcatggacctggagaaacgccatgtgctgggtcgcctgattaccgtgaacccgattgtgacc gagaaagatagcccggtgaacattgaagccgaaccgccgttcggcgatagctacattatcattggtgttgaagc agctgaactgaaactgaactggttcaagaagggcagcagcattggccagcatcatcatcatcatcatcatcatt aa Ala3 (SEQ ID NO: 13):
gactacaaggatgatgacgacaaaggcagcggcatgagctatagcatgtgcaccggcaaatttaaaatcgtgaa agagatcgccgcagctcaagctggtaccattgtgatccgtgtgcagtatgaaggcgatggtagcccgtgcaaaa tcccgttcgagatcatggacctggagaaacgccatgtgctgggtcgcctgattaccgtgaacccgattgtgacc gagaaagatagcccggtgaacattgaagccgaaccgccgttcggcgatagctacattatcattggtgctgcagc aggtgcactggaactgaactggttcaagaagggcagcagcattggccagcatcatcatcatcatcatcatcatt aa Ala5 (SEQ ID NO: 14):
gactacaaggatgatgacgacaaaggcagcggcatgagctatagcatgtgcaccggcaaatttaaaatcgtgaa agagatcgccgcaactgcagatgctaccattgtgatccgtgtgcagtatgaaggcgatggtagcccgtgcaaaa tcccgttcgagatcatggacctggagaaacgccatgtgctgggtcgcctgattaccgtgaacccgattgtgacc gagaaagatagcccggtgaacattgaagccgaaccgccgttcggcgatagctacattatcattggtgctgaagc agctccactgacactgaactggttcaagaagggcagcagcattggccagcatcatcatcatcatcatcatcatt aa Ala11 (SEQ ID NO: 15):
gactacaaggatgatgacgacaaaggcagcggcatgagctatagcatgtgcaccggcaaatttaaaatcgtgaa agagatcgccgaagctgcacctggtaccattgtgatccgtgtgcagtatgaaggcgatggtagcccgtgcaaaa tcccgttcgagatcatggacctggagaaacgccatgtgctgggtcgcctgattaccgtgaacccgattgtgacc gagaaagatagcccggtgaacattgaagccgaaccgccgttcggcgatagctacattatcattggtgctgaacc -continued aggtgaactgacactgaactggttcaagaagggcagcagcattggccagcatcatcatcatcatcatcatcatt aa Ala30 (SEQ ID NO: 16):
gactacaaggatgatgacgacaaaggcagcggcatgagctatagcatgtgcaccggcaaatttaaaatcgtgaa agagatcgccgaaactcaagatggtaccattgtgatccgtgtgcagtatgaaggcgatggtagcccgtgcaaaa tcccgttcgagatcatggacctggagaaacgccatgtgctgggtcgcctgattaccgtgaacccgattgtgacc gagaaagatagcccggtgaacattgaagccgaaccgccgttcggcgatagctacattatcattggtgctgaacc agctgcactggaactgaactggttcaagaagggcagcagcattggccagcatcatcatcatcatcatcatcatt aa.

Shown below are the DIII wildtype amino acid sequences for serotypes DENV-1 (SEQ ID NO:17), DENV-2 (SEQ ID NO:18), DENV-3 (SEQ ID NO:19) and DENV-4 (SEQ ID NO:20). Also shown are the AB loop and FG loop regions. The arrow next to A is the A-strand, and the arrow next to G is the G-strand. The A/G strand is amino acid residues under the A and G arrows.

```
                        AB loop

             A                  B
            300         310         320
DENV-1 GMSYVMCTGSFKLEKEVAETQHGTVLVQVKYEGTD
DENV-2 GMSYSMCTGKFKIVKEIAETQHGTIVIRVQYEGDG
DENV-3 GMSYAMCLNTFVLKKEVSETQHGTILIKVEYKGED
DENV-4 GMSYTMCSGKFSIDKEMAETQHGTTVVKVKYEGAG

           C               D               E
       331         340        350         360
DENV-1 APCKIPFSTQDEKGVTQNGRLITANPIVTDKEKPV
DENV-2 SPCKIPFEIMDLEKRHVLGRLITVNPIVTEKDSPV
DENV-3 APCKIPFSTEDGQGKAHNGRLITANPVVTKKEEPV
DENV-4 APCKVPIEIRDVNKEKVVGRIISSTPFAENTNSVT

              F               G
            370         380         390
DENV-1 NIETEPPFGESYIIVGAGEKALKLSWFKKGSSIGK
DENV-2 NIEAEPPFGDSYIIIGVEPGQLKLNWFKKGSSIGQ
DENV-3 NIEAEPPFGESNIVIGIGDKALKINWYKKGSSIGK
DENV-4 NIELEPPFGDSYIVIGVGDSALTLHWFRKGSSIGK

                        FG loop
```

Strands indicated with arrows

Also provided are DIII variants encoded by the nucleic acid set forth in SEQ ID NO:9, SEQ ID NO:10, SEQ ID NO:11, SEQ ID NO:12, SEQ ID NO:13, SEQ ID NO:14, SEQ ID NO:15, and SEQ ID NO: 16.

Further provided are dimers and oligomers comprising any of the variants disclosed herein. The dimer or oligomer can contain a C-terminal disulfide-bonded leucine zipper dimerization domain (41). Stimulation of B-cell receptors (BCRs) for affinity maturation requires cross-linking of BCRs and thus, dimers or higher order oligomers may be beneficial. In addition, the serum stability of dimers and higher order oligomers may be better than monomers because of the increased size, which minimizes renal clearance, and potential resistance to degradation.

Also provided is a virion of an isolated, recombinant Dengue virus comprising any of the variants or dimers or oligomers disclosed herein.

Also provided is a Dengue virus vaccine composition comprising any of the variants, or dimers or oligomers, or virions disclosed herein. The vaccine composition can further comprise an immunological adjuvant.

Also provided is a method of eliciting an immune response in a subject comprising administering to the subject any of the variants, or dimers or oligomers, or virions, or vaccines disclosed herein in an amount effective to elicit an immune response in a subject.

Also provided is a method of vaccinating a subject for Dengue virus infection comprising administering to the subject any of the variants, or dimers or oligomers, or virions, or vaccines disclosed herein in an amount effective to vaccinate a subject for Dengue virus.

Also provided is a method of immunizing a subject against Dengue virus infection comprising administering to the subject any of the variants, or dimers or oligomers, or virions, or vaccines disclosed herein in an amount effective to immunize a subject against Dengue virus.

Also provided is a method of treating a Dengue virus infection in a subject or treating a disease caused by a Dengue virus infection in a subject comprising administering to the subject any of the variants, or dimers or oligomers, or virions, or vaccines disclosed herein in an amount effective to treat a Dengue virus infection or treat a disease caused by a Dengue virus infection in a subject. The subject being treated can have, for example, one or more of Dengue Hemorrhagic Fever (DHF) and Dengue Shock Syndrome (DSS).

Preferably, the variants, dimers, oligomers, virions and vaccines disclosed herein are effective against all Dengue virus serotypes.

Also provided is a method of preparing a Dengue virus glycoprotein subunit E DIII variant that is effective as a Dengue virus immunogen, the method comprising a) masking immunodominant, but non-neutralizing or Dengue virus type-specific, AB- and FG-loops of DIII by mutation to obtain a DIII variant, which retains the A/G strand, and b) using phage display to select a DIII variant from step a) that elicits an antibody targeting a broadly neutralizing antibody epitope, thereby preparing a Dengue virus glycoprotein subunit E DIII variant that is effective as a Dengue virus immunogen.

In the method, the amino acid positions in DIII can be varied, for example, by substitution with alanine or serine. The variant can be subjected to selection against a DIII-specific broadly neutralizing A/G strand monoclonal antibody. Preferably, the variant binds to a DIII-specific broadly neutralizing A/G strand monoclonal antibody with similar reactivity as wild type DIII, but the variant does not exhibit reactivity to an AB-loop monoclonal antibody or to a FG-loop monoclonal antibody.

The vaccine or composition for administration to a subject can be formulated for administration by any routine route of administration, including but not limited to, subcutaneous, intra-muscular, intra-nasal, or mucosal administration.

The subject can be any animal, and is preferably a human subject.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

Experimental Details

An attractive strategy for next-generation platforms or boosting agents is the use of subunit vaccines (immunogens) that contain all or parts of the Dengue virus glycoprotein subunit E. The use of recombinant protein immunogens prevents the premature clearance of attenuated or chimeric virus boosters due to pre-existing immunity to vaccine vector components; such clearance would render the boost less effective. Furthermore, subunit vaccines are safer and have lower risk of inducing infection-related side effects because they are replication incompetent.

The major challenge to the use of the Dengue virus glycoprotein E domain III (EDIII) as a single immunogen is that the immunodominant regions are focused on non-productive or narrow-spectrum epitopes. Protein engineering was used to identify and characterize EDIII variants that overcome these limitations. Furthermore, by re-engineering EDIII to elicit antibodies targeting a bNAb epitope, the present strategy achieves a single component immunogen that elicits protective antibodies, avoiding the manufacturing and possible safety concerns of multivalent immunogen production. The present application discloses protein immunogens based on the Dengue virus glycoprotein E domain III (EDIII).

Major advances in combinatorial and computational protein design have previously permitted engineering of proteins with enhanced function. "Synthetic protein engineering"—defined here as use of phage- or yeast-displayed libraries with restricted diversity elements encoded by designed, synthetic oligonucleotides—in particular has been used in a variety of applications (32-38). The combination of highly specified libraries, coupled with complete control of the binding selections, provides the opportunity to develop reagents that have either enhanced specificity for a single target (e.g., for particular post-translational modifications) or multi-specificity without being non-specific. This method has been used to identify highly specific binding antibodies or proteins that generally would not be accessible by other methods (32-34, 36). For example, specific fusogenic intermediates of virus glycoproteins have been targeted by this approach.

In the present studies, phage display and synthetic protein engineering were used to develop novel "resurfaced" variants of DENV2 EDIII (rsDIII) in which the immunodominant AB- and FG-loops, as well as other surface positions, are masked by mutation. DENV2 EDIII was expressed in bivalent format on M13 bacteriophage as a fusion to the minor coat protein (pIII). Based on the structure of EDIIIs from DENV1-4 in complex with 4E11, as well as on previous "functional epitope" mapping to decipher the major contributing residues to binding 4E11, two libraries were designed in which selected positions in DENV2 EDIII were allowed to vary among wild type (WT) and alanine (Ala) (Ala library) or WT and serine (Ser) (Ser library) (FIG. 1A). The varied positions included all immunodominant regions of the AB- and FG-loops as well as several surface exposed residues distal to the A/G strands. Alanine was chosen as a substitution because it is statistically disfavored at antibody-antigen interfaces, likely due to the relatively short side chain that is incapable of participating in extended interactions required for large intermolecular interfaces (39). Serine contains a small, flexible, and relatively inert side chain and is also unlikely to form extended interactions with antibody combining sites (40). These two libraries were subjected to selection against 4E11. It was hypothesized that mutants from these libraries that survived selection for 4E11 binding would retain productive conformation for the A/G strand epitope. Clones were sought that had a high content of Ala or Ser in the varied positions, to destroy unproductive epitopes, but retained 4E11 binding thereby maintaining the critical neutralizing epitope.

Figure 1B:
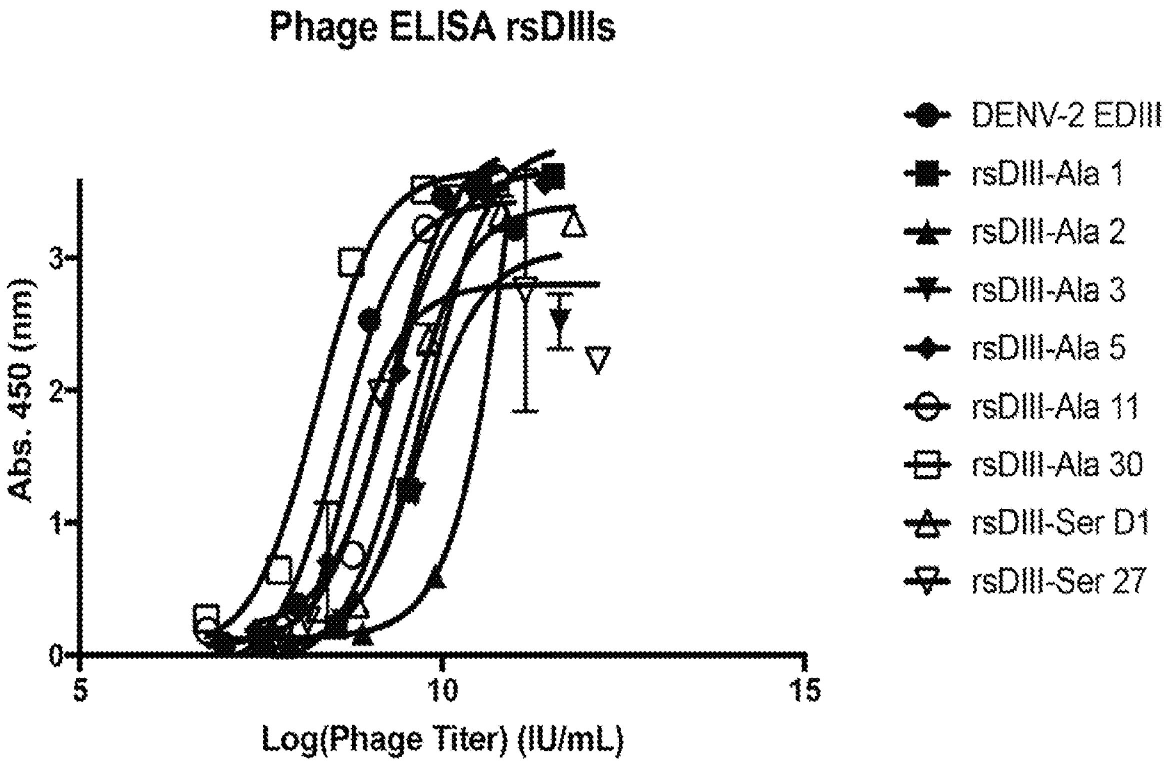
Figure 1C:
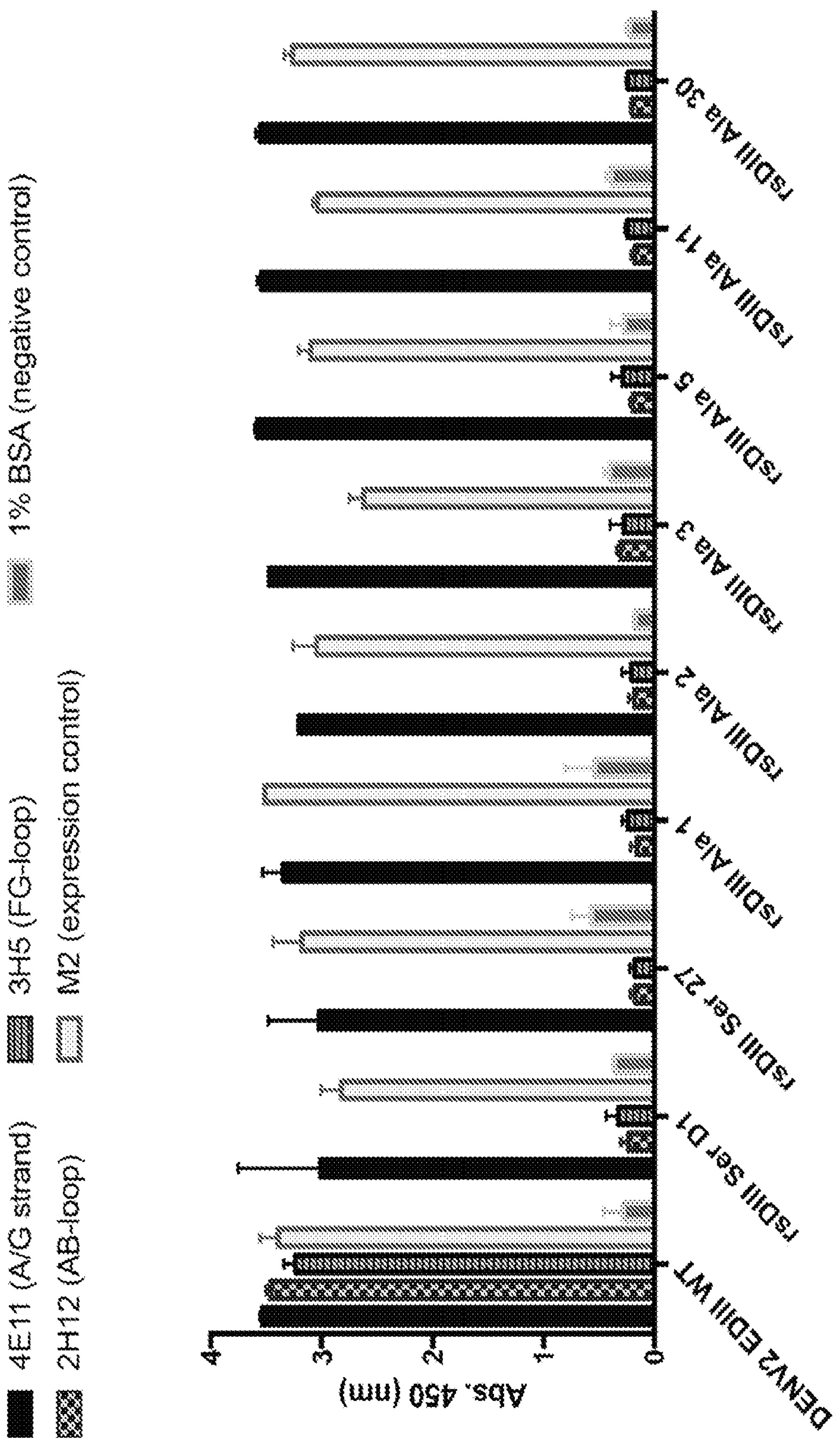

From these selections, eight rsDIII clones were identified (six from the Ala library and two from the Ser library) with desirable reactivity profiles (Table 1). Phage ELISA showed that all rsDIIIs bound to immobilized 4E11 with similar reactivity to WT DENV2 EDIII (FIG. 1B). Importantly, none of the rsDIIIs exhibited reactivity at high phage titer to the prototypic AB-loop mAb 2H12 (non-neutralizing) (27) or the prototypic FG-loop mAb 3H5-1 (type-specific) (26), whereas WT DENV2 EDIII did (FIG. 1C). The expression levels of all rsDIIIs were similar as determined by reactivity with mAb M2, which specifically recognizes the FLAG epitope that was engineered at the N-terminus of EDIII.

Figure 2A:
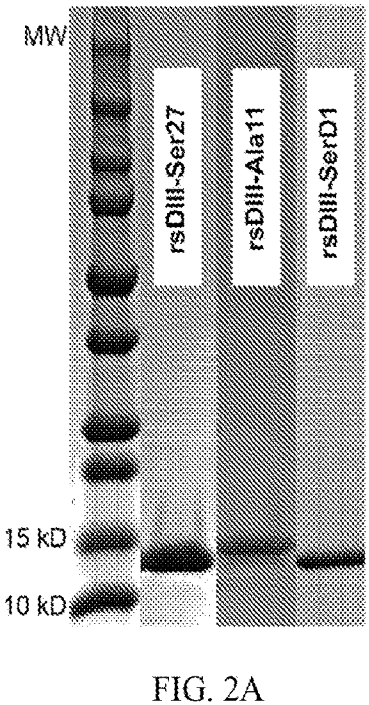
FIG. 2A-2B. (A) Sample SDS-PAGE purification of rsDIIIs. A single product at the expected mass (15 kD) is observed. (B) ELISA profile for binding of purified DENV2 EDIII WT or rsDIII-Ser27 to either 4E11 or 1% BSA.
Figure 2B:
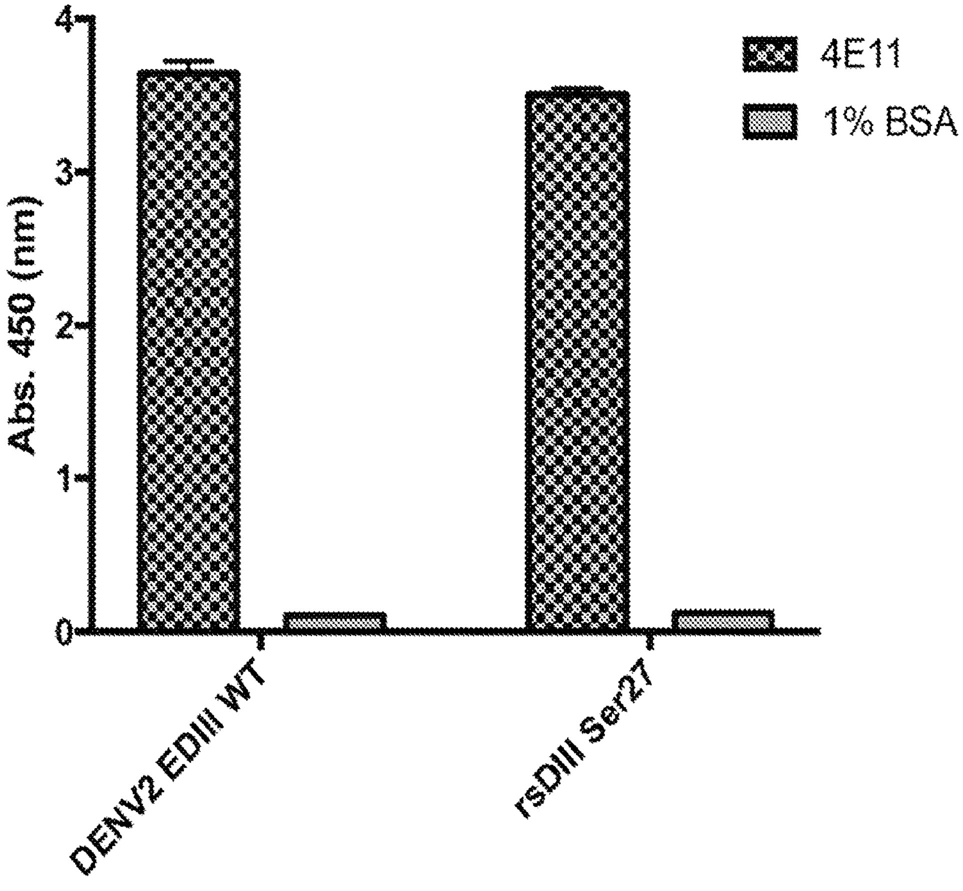

The most efficient production protocol was found to involve purification by Nickel affinity chromatography and refolding of rsDIIIs from inclusion bodies, which generally yields high purity material in reasonable yield (see FIG. 2A, for SDS-PAGE analysis). Importantly, the activity of one refolded rsDIII protein (rsDIII-Ser27) for binding to 4E11 has been confirmed (FIG. 2B), indicating that protein behavior off-phage is similar to behavior on-phage.

TABLE 1

Sequences of Selected rsDIII Clones.

| Clone/ | AB loop | | | | | | | FG loop | | | | | | |
|---|---|---|---|---|---|---|---|---|---|---|---|---|---|---|
| Position | 314 | 315 | 316 | 317 | 318 | 329 | 334 | 381 | 382 | 383 | 384 | 385 | 386 | 388 |
| WT DENV-2 EDIII | E | T | Q | H | G | D | K | G | V | E | P | G | Q | K |

TABLE 1-continued

Sequences of Selected rsDIII Clones.

| Clone/ Position | AB loop 314 | 315 | 316 | 317 | 318 | 329 | 334 | FG loop 381 | 382 | 383 | 384 | 385 | 386 | 388 |
|---|---|---|---|---|---|---|---|---|---|---|---|---|---|---|
| rsDIII-Ala1 | A | A | A | A | G | D | K | G | V | A | P | G | Q | *E* |
| rsDIII-Ala2 | A | A | A | *D* | A | D | *E* | G | V | E | A | A | *E* | K |
| rsDIII-Ala3 | A | A | Q | A | G | D | K | G | A | A | A | G | A | *E* |
| rsDIII-Ala5 | A | T | A | *D* | A | D | K | G | A | E | A | A | *P* | *T* |
| rsDIII-Ala11 | E | A | A | *P* | G | D | K | G | A | E | P | G | *E* | *T* |
| rsDIII-Ala30 | E | T | Q | *D* | G | D | K | G | A | E | P | A | A | *E* |
| rsDIII-SerD1 | E | S | S | S | G | *Y* | K | G | V | E | S | *A* | Q | K |
| rsDIII-Ser27 | S | T | S | H | G | D | K | G | V | E | S | S | Q | S |

Residues substituted for Ala (A) or Ser S) are shown by underlining with a straight line. The combinatorial codon permitted additional variation, in some cases these residues were selected, shown in italics and underlining with a wavy underline. The amino acid residues in Table 1 correspond to the underlined portions of the corresponding parts of the amino acid sequences of the variants disclosed herein above: Ser27 (SEQ ID NO:1), SerD1 (SEQ ID NO:2), Ala1 (SEQ ID NO:3), Ala2 (SEQ ID NO:4), Ala3 (SEQ ID NO:5), Ala5 (SEQ ID NO:6), Ala11 (SEQ ID NO:7), and Ala30 (SEQ ID NO:8). The wildtype DENV-2 DIII sequence is shown in SEQ ID NO:18.

A number of the "resurfaced" DIIIs (rsDIIIs, vaccine candidates) have been expressed, purified, and characterized in greater detail. Among these, the clones rsDIII-Ala11 and rsDIII-Ala30 had favorable properties, and thus additional experiments were conducted with these two clones.

Figures 3A, 3B, 3C:
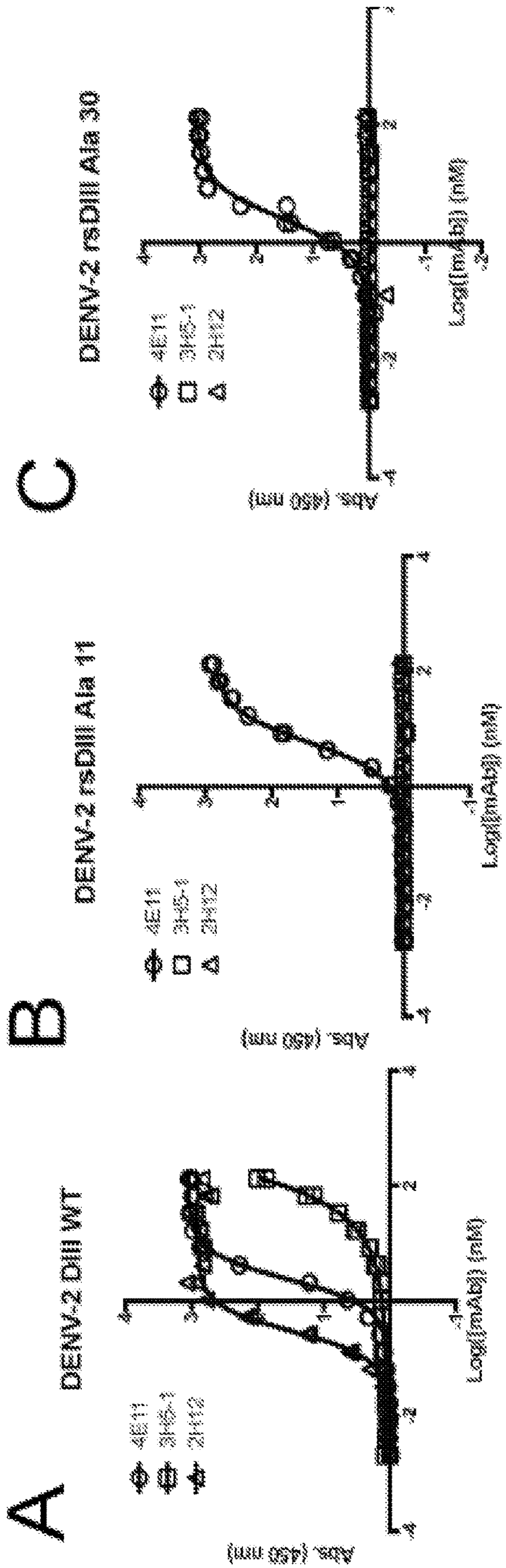
FIG. 3A-3C. WT DENV2 DIII (A) and clones rsDIII-Ala11 (B) and rsDIII-Ala30 (C) bind to the model broadly neutralizing antibody 4E11, but the clones do not appreciably bind to 2H12, a prototypic AB-loop antibody (non-neutralizing epitope) or to 3H5-1, a prototypic FG-loop antibody (type-specific).

Binding of rsDIII-Ala11 and rsDIII-Ala30 to the model broadly neutralizing antibody (bNAb) 4E11 was found to be as good as WT DENV2 DIII, but importantly the rsDIII-Ala11 and rsDIII-Ala30 clones did not exhibit appreciable binding to 2H12, a prototypic AB-loop antibody (non-neutralizing epitope) or 3H5-1, a prototypic FG-loop antibody (type-specific) (FIG. 3A-3C). The results in Table 2 were obtained by ELISA.

TABLE 2

EC50 values for binding of DIII domains to DENV mAbs.

| | 4E11 | 2H12 | 3H5 |
|---|---|---|---|
| WT DENV2 DIII | 2.4 nM | 0.32 nM | ~μM |
| rsDIII-Ala11 | 5.7 nM | No binding | No binding |
| rsDIII-Ala30 | 2.5 nM | No binding | No binding |

Figure 4:
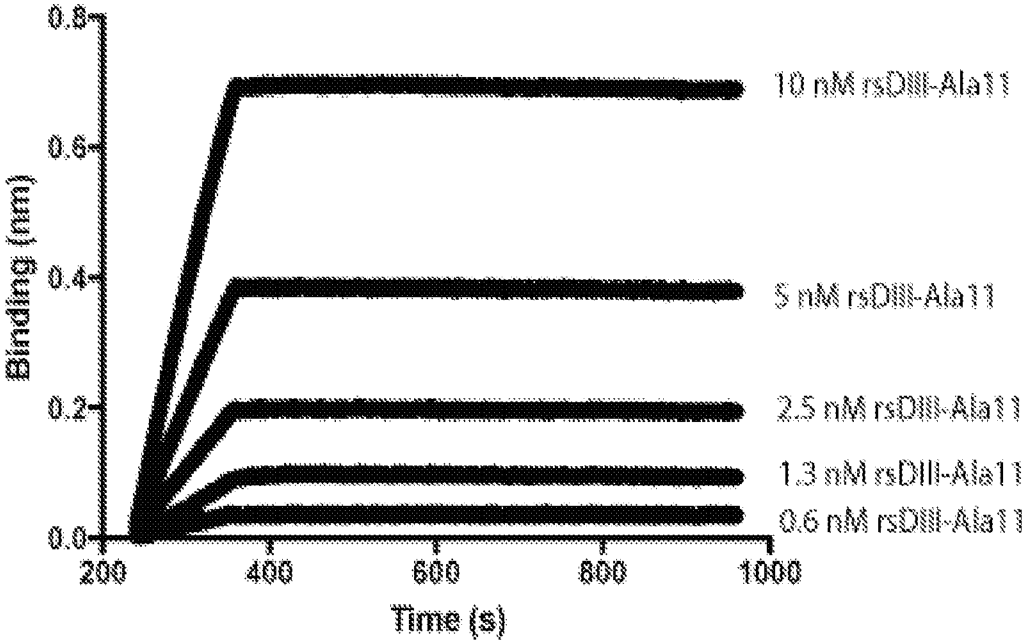
FIG. 4. rsDIII-A11 binding to mAb 4E11 by biolayer interferometry.

By biolayer interferometry, rsDIII-Ala30 was also found to bind with similar high affinity to 4E11 but not to 2H12 or 3H5-1. Similar results were obtained with rsDIII-Ala11 (FIG. 4, Table 3).

TABLE 3

DIII binding to DENV mAbs, by biolayer interferometry and ELISA.

| Clone | mAb 4E11 (A/G strand) BLI ($K_D$) | ELISA ($EC_{50}$) | mAb 2H12 (AB loop) BLI ($K_D$) | ELISA ($EC_{50}$) | mAb 3H5-1 (FG loop) ELISA ($EC_{50}$) |
|---|---|---|---|---|---|
| WT DENV2 EDIII | ~4 pM | 2 nM | 30 pM | 0.3 nM | ~2 mM |
| rsDIII-Ala11 | <1 pM | 6 nM | No binding | No binding | No binding |

NMR experiments were performed with 15N-labeled WT DENV2 EDIII, rsDIII-Ala11, and rsDIII-Ala30. 1H-15N HSQC data shows that many resonances corresponding to "core" residues overlap between WT and either rsDIII-Ala11 or rsDIII-Ala30. These data indicate that the core structures of WT, rsDIII-Ala111 and rsDIII-Ala30 are likely to be very similar, and thus the epitope resurfacing has not affected the core folding structure of the DIII domain.

Figure 5A:
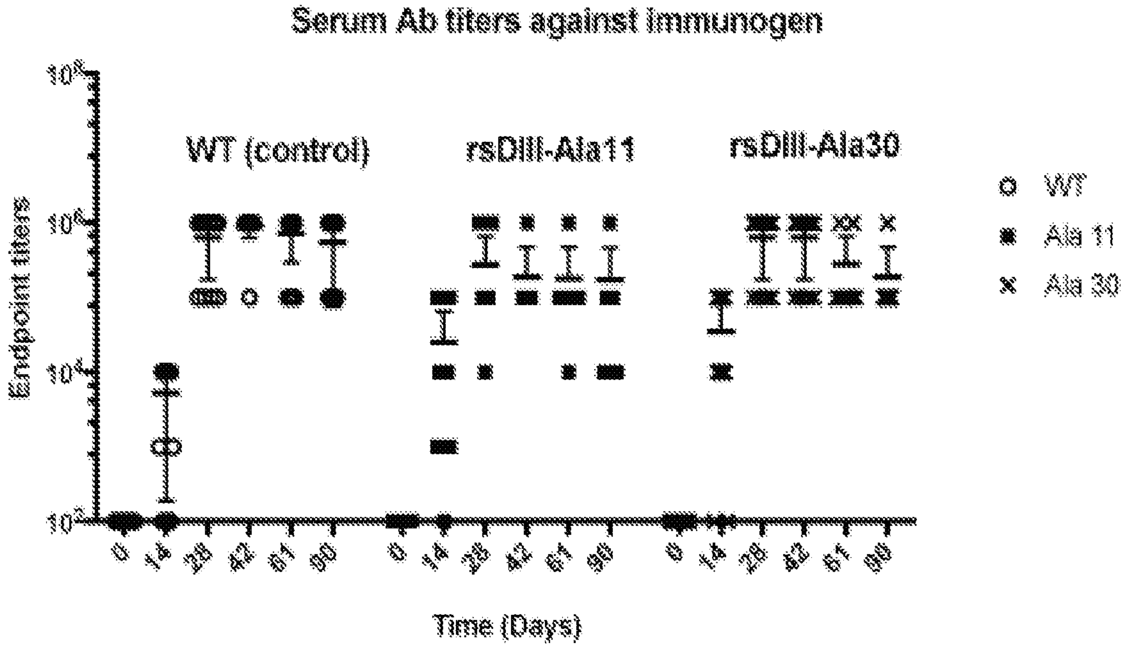
FIG. 5A-5B. Serum Ab titers against immunogens. (A) rsDIII-Ala11 and rsDIII-Ala30 immunogens result in similarly robust antibody responses compared to WT DENV-2 DIII. (B) No activity was observed against a negative control (his-tagged).
Figure 5B:
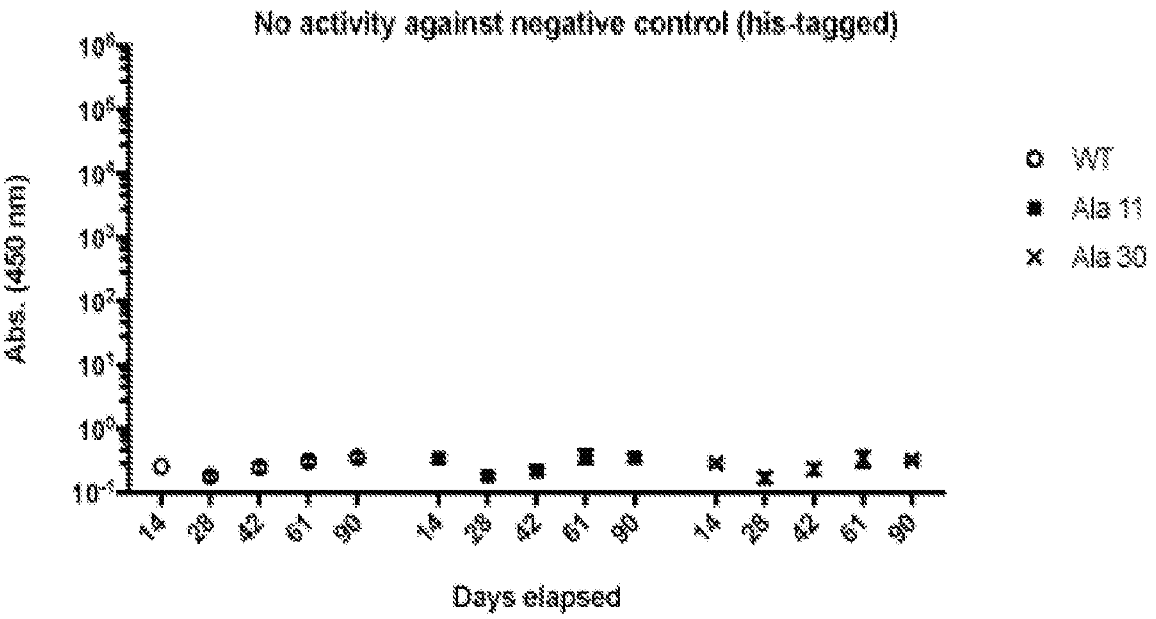
Figure 6:
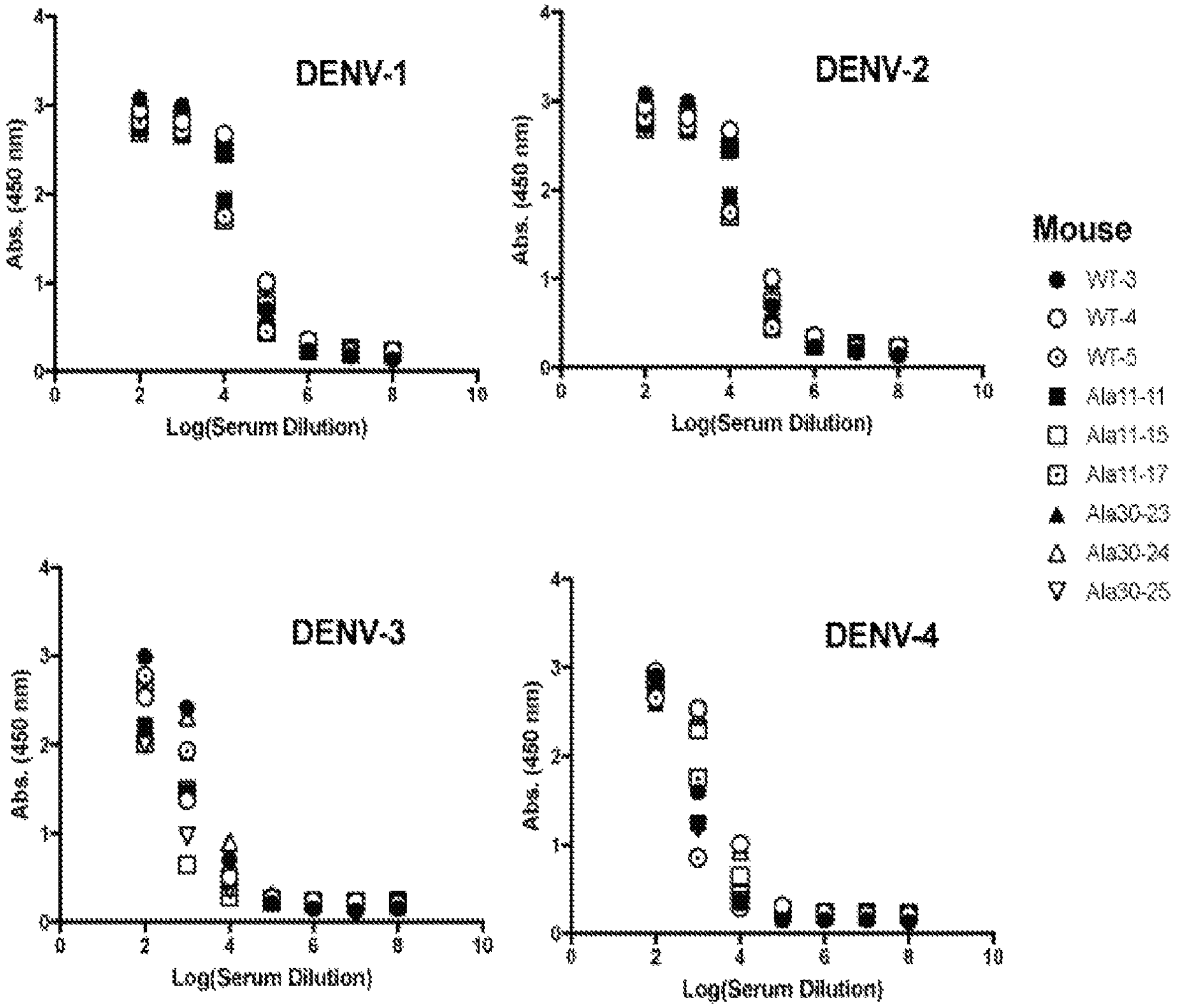
FIG. 6. Reactivity of rsDIIIs was found to be broad for DIIIs from all four serotypes DENV-1, DENV-2, DENV-3 and DENV-4.

In vivo testing. Groups of 10 BALB/c mice were immunized with three doses of WT DENV2 EDIII, rsDIII-Ala11, or rsDIII-Ala30. Mice were immunized with immuogen at days 0 (20 μg/Complete Freund's Adjuvant, CFA), day 14 (20 μg/CFA), and day 28 (10 μg/Incomplete Freund's Adjuvant, IFA). Sera were analyzed at days 0 (naïve, pre-immune sera), 14, 28, 42, 61, and 90. All three immunogens were found to elicit robust antibody responses (high titers) that were specific for DIII (activity against non-specific control bearing a His tag, which is also present in DIII, was not observed) (FIG. 5A-5B). Furthermore, the reactivity of rsDIII-Ala11 and rsDIII-Ala30 was found to be broad for DIII from all four serotypes (DENV-1, DENV-2, DENV-3 and DENV-4) (FIG. 6). Notably, this same cross-reactivity was observed with WT DENV2 EDIII, although this has been documented previously as a predominant response to the AB loop, which is extensively mutagenized in rsDIII-Ala11 and rsDIII-Ala30.

Examples of purification protocols include the following.

rsDIII Expression.

From a freshly transformed plate, incubate 1 colony in 50 mL 2×YT media with 50 μL carbenicillin overnight at 37° C., 220 RPM. Transfer 5 mL overnight culture to 100 mL low phosphate media with 100 μL carbenicillin; make up to ten 100 mL cultures. Incubate for 24 hours at 30° C., 220 RPM. Harvest cells via centrifugation at 4,500 RPM, 4° C., for 15 minutes. Weigh cell pellets and freeze at −20° C. until purification.

rsDIII Purification.

Thaw cells at room temperature. Per gram of wet cell weight add 5 mL of 1×-diluted Bug Buster. Resuspend cells in PBS (20 mM sodium phosphate monobasic+150 mM NaCl) with EDTA-free protease cocktail inhibitor and DNaseI. Add 10× Bug Buster to dilute to 1× and incubate with gentle rocking for 20 minutes at room temperature. Centrifuge at 12,000 RPM (ss-34), for 30 minutes at 4° C. Rinse the pellet (inclusion body fraction) with PBS by vortexing and centrifuge for 30 minutes at 12,000 RPM and 4° C. Discard supernatant. Resuspend pellet in 8M urea/PBS overnight with stirring. Spin down at 15° C. for 30 minutes at 12,000 RPM. Keep the supernatant (solubilized inclusion body).

Wash 1 mL Ni-NTA beads (Qiagen) with 8M urea/PBS. Load inclusion body fraction onto the column and collect the flow through. Wash with 7.5 mL 8M urea/PBS, pH 6.0 and collect fraction. Wash with 7.5 mL 8M urea/PBS, pH 5.3/55 mM Imidazole and collect fraction. Elute with 3.8 mL 8M urea/PBS, pH 4.0/250 mM Imidazole and collect elute. Elute with 5 mL 8M urea/PBS, pH 4.0/500 mM Imidazole and collect elute. Run SDS-PAGE to verify purity and pool relevant fractions.

rsDIII Refolding.

Dilute denatured rsDIII 20-fold into 20 mM Tris-HCl, 500 mM NaCl, pH 7.8—results in a final urea concentration of 0.4M. Dialyze sample in 20 mM Tris-HCl, 500 mM NaCl, pH 7.8 to remove urea.

rsDIII Purification and Refolding on Column.

Prepare inclusion body fraction as above and wash 1 mL Ni-NTA beads as above. Load inclusion body fraction onto column and collect the flow through. Wash with 5 mL 8M urea/PBS, pH 6.0 and collect fraction. Wash with 5 mL 8M urea/PBS, pH 5.8 and collect fraction. Wash with 10×1 mL refolding buffer (20 mM Tris-HCl, 500 mM NaCl, pH 7.8) and collect fraction. Elute with 5 mL 20 mM Tris/500 mM NaCl/250 mM Imidazole, pH 7.8 and collect elute. Elute with 5 mL 20 mM Tris/500 mM NaCl/500 mM Imidazole, pH 7.8 and collect elute. Run SDS-PAGE and pool relevant fractions. Concentrate to 2-3 mL and dialyze into 20 mM Tris-HCl/500 mM NaCl, pH 7.8 to remove imidazole.

REFERENCES

1. Bhatt, S., Gething, P. W., Brady, O. J., Messina, J. P., Farlow, A. W., Moyes, C. L., Drake, J. M., Brownstein, J. S., Hoen, A. G., Sankoh, O., Myers, M. F., George, D. B., Jaenisch, T., Wint, G. R., Simmons, C. P., Scott, T. W., Farrar, J. J., and Hay, S. I. (2013) The global distribution and burden of dengue. *Nature* 496, 504-507
2. Kraemer, M. U., Sinka, M. E., Duda, K. A., Mylne, A. Q., Shearer, F. M., Barker, C. M., Moore, C. G., Carvalho, R. G., Coelho, G. E., Van Bortel, W., Hendrickx, G., Schaffner, F., Elyazar, I. R., Teng, H. J., Brady, O. J., Messina, J. P., Pigott, D. M., Scott, T. W., Smith, D. L., Wint, G. R., Golding, N., and Hay, S. I. (2015) The global distribution of the arbovirus vectors *Aedes aegypti* and *Ae. albopictus. eLife* 4, e08347
3. Guzman, M. G., Alvarez, M., and Halstead, S. B. (2013) Secondary infection as a risk factor for dengue hemorrhagic fever/dengue shock syndrome: an historical perspective and role of antibody-dependent enhancement of infection. *Archives of virology* 158, 1445-1459
4. Hadinegoro, S. R., Arredondo-Garcia, J. L., Capeding, M. R., Deseda, C., Chotpitayasunondh, T., Dietze, R., Muhammad Ismail, H. I., Reynales, H., Limkittikul, K., Rivera-Medina, D. M., Tran, H. N., Bouckenooghe, A., Chansinghakul, D., Cortes, M., Fanouillere, K., Forrat, R., Frago, C., Gailhardou, S., Jackson, N., Noriega, F., Plennevaux, E., Wartel, T. A., Zambrano, B., and Saville, M. (2015) Efficacy and Long-Term Safety of a Dengue Vaccine in Regions of Endemic Disease. *The New England journal of medicine* 373, 1195-1206
5. Osorio, J. E., Velez, I. D., Thomson, C., Lopez, L., Jimenez, A., Haller, A. A., Silengo, S., Scott, J., Boroughs, K. L., Stovall, J. L., Luy, B. E., Arguello, J., Beatty, M. E., Santangelo, J., Gordon, G. S., Huang, C. Y., and Stinchcomb, D. T. (2014) Safety and immunogenicity of a recombinant live attenuated tetravalent dengue vaccine (DENVax) in flavivirus-naive healthy adults in Colombia: a randomised, placebo-controlled, phase 1 study. *The Lancet. Infectious diseases* 14, 830-838
6. Kirkpatrick, B. D., Durbin, A. P., Pierce, K. K., Carmolli, M. P., Tibery, C. M., Grier, P. L., Hynes, N., Diehl, S. A., Elwood, D., Jarvis, A. P., Sabundayo, B. P., Lyon, C. E., Larsson, C. J., Jo, M., Lovchik, J. M., Luke, C. J., Walsh, M. C., Fraser, E. A., Subbarao, K., and Whitehead, S. S. (2015) Robust and Balanced Immune Responses to All 4 Dengue Virus Serotypes Following Administration of a Single Dose of a Live Attenuated Tetravalent Dengue Vaccine to Healthy, Flavivirus-Naive Adults. *The Journal of infectious diseases* 212, 702-710
7. Kuhn, R. J., Zhang, W., Rossmann, M. G., Pletnev, S. V., Corver, J., Lenches, E., Jones, C. T., Mukhopadhyay, S., Chipman, P. R., Strauss, E. G., Baker, T. S., and Strauss, J. H. (2002) Structure of dengue virus: implications for flavivirus organization, maturation, and fusion. *Cell* 108, 717-725
8. Modis, Y., Ogata, S., Clements, D., and Harrison, S. C. (2003) A ligand-binding pocket in the dengue virus envelope glycoprotein. *Proceedings of the National Academy of Sciences of the United States of America* 100, 6986-6991
9. Modis, Y., Ogata, S., Clements, D., and Harrison, S. C. (2004) Structure of the dengue virus envelope protein after membrane fusion. *Nature* 427, 313-319
10. Chiu, M. W., and Yang, Y. L. (2003) Blocking the dengue virus 2 infections on BHK-21 cells with purified recombinant dengue virus 2 E protein expressed in *Escherichia coli. Biochemical and biophysical research communications* 309, 672-678
11. Watterson, D., Kobe, B., and Young, P. R. (2012) Residues in domain III of the dengue virus envelope glycoprotein involved in cell-surface glycosaminoglycan binding. *The Journal of general virology* 93, 72-82
12. Huerta, V., Chinea, G., Fleitas, N., Sarria, M., Sanchez, J., Toledo, P., and Padron, G. (2008) Characterization of the interaction of domain III of the envelope protein of dengue virus with putative receptors from CHO cells. *Virus research* 137, 225-234
13. Dejnirattisai, W., Wongwiwat, W., Supasa, S., Zhang, X., Dai, X., Rouvinski, A., Jumnainsong, A., Edwards, C., Quyen, N. T., Duangchinda, T., Grimes, J. M., Tsai, W. Y., Lai, C. Y., Wang, W. K., Malasit, P., Farrar, J., Simmons, C. P., Zhou, Z. H., Rey, F. A., Mongkolsapaya, J., and Screaton, G. R. (2015) A new class of highly potent, broadly neutralizing antibodies isolated from viremic patients infected with dengue virus. *Nature immunology* 16, 170-177

14. Rouvinski, A., Guardado-Calvo, P., Barba-Spaeth, G., Duquerroy, S., Vaney, M. C., Kikuti, C. M., Navarro Sanchez, M. E., Dejnirattisai, W., Wongwiwat, W., Haouz, A., Girard-Blanc, C., Petres, S., Shepard, W. E., Despres, P., Arenzana-Seisdedos, F., Dussart, P., Mongkolsapaya, J., Screaton, G. R., and Rey, F. A. (2015) Recognition determinants of broadly neutralizing human antibodies against dengue viruses. *Nature* 520, 109-113
15. Cockburn, J. J., Sanchez, M. E. N., Fretes, N., Urvoas, A., Staropoli, I., Kikuti, C. M., Coffey, L. L., Seisdedos, F. A., Bedouelle, H., and Rey, F. A. (2012) Mechanism of dengue virus broad cross-neutralization by a monoclonal antibody. *Structure* 20, 303-314
16. Lok, S. M., Kostyuchenko, V., Nybakken, G. E., Holdaway, H. A., Battisti, A. J., Sukupolvi-Petty, S., Sedlak, D., Fremont, D. H., Chipman, P. R., Roehrig, J. T., Diamond, M. S., Kuhn, R. J., and Rossmann, M. G. (2008) Binding of a neutralizing antibody to dengue virus alters the arrangement of surface glycoproteins. *Nature structural & molecular biology* 15, 312-317
17. Frei, J. C., Kielian, M., and Lai, J. R. (2015) Comprehensive mapping of functional epitopes on dengue virus glycoprotein E DIII for binding to broadly neutralizing antibodies 4E11 and 4E5A by phage display. *Virology* 485, 371-382
18. Suzarte, E., Gil, L., Valdes, I., Marcos, E., Lazo, L., Izquierdo, A., Garcia, A., Lopez, L., Alvarez, M., Perez, Y., Castro, J., Romero, Y., Guzman, M. G., Guillen, G., and Hermida, L. (2015) A novel tetravalent formulation combining the four aggregated domain III-capsid proteins from dengue viruses induces a functional immune response in mice and monkeys. *International immunology* 27, 367-379
19. Gil, L., Marcos, E., Izquierdo, A., Lazo, L., Valdes, I., Ambala, P., Ochola, L., Hitler, R., Suzarte, E., Alvarez, M., Kimiti, P., Ndung'u, J., Kariuki, T., Guzman, M. G., Guillen, G., and Hermida, L. (2015) The protein DIIIC-2, aggregated with a specific oligodeoxynucleotide and adjuvanted in alum, protects mice and monkeys against DENV-2. *Immunology and cell biology* 93, 57-66
20. Izquierdo, A., Garcia, A., Lazo, L., Gil, L., Marcos, E., Alvarez, M., Valdes, I., Hermida, L., Guillen, G., and Guzman, M. G. (2014) A tetravalent dengue vaccine containing a mix of domain III-P64k and domain III-capsid proteins induces a protective response in mice. *Archives of virology* 159, 2597-2604
21. Garcia-Machorro, J., Lopez-Gonzalez, M., Barrios-Rojas, O., Femandez-Pomares, C., Sandoval-Montes, C., Santos-Argumedo, L., Villegas-Sepulveda, N., Gutierrez-Castaneda, B., and Cedillo-Barron, L. (2013) DENV-2 subunit proteins fused to CR2 receptor-binding domain (P28)-induces specific and neutralizing antibodies to the Dengue virus in mice. *Human vaccines & immunotherapeutics* 9, 2326-2335
22. Li, X.-Q., Qiu, L.-W., Chen, Y., Wen, K., Cai, J.-P., Chen, J., Pan, Y.-X., Li, J., Hu, D.-M., and Huang, Y.-F. (2013) Dengue virus envelope domain III immunization elicits predominantly cross-reactive, poorly neutralizing antibodies localized to the AB loop: implications for dengue vaccine design. *Journal of General Virology* 94, 2191-2201
23. Chen, H. W., Liu, S. J., Li, Y. S., Liu, H. H., Tsai, J. P., Chiang, C. Y., Chen, M. Y., Hwang, C. S., Huang, C. C., Hu, H. M., Chung, H. H., Wu, S. H., Chong, P., Leng, C. H., and Pan, C. H. (2013) A consensus envelope protein domain III can induce neutralizing antibody responses against serotype 2 of dengue virus in non-human primates. *Archives of virology* 158, 1523-1531
24. Arora, U., Tyagi, P., Swaminathan, S., and Khanna, N. (2013) Virus-like particles displaying envelope domain III of dengue virus type 2 induce virus-specific antibody response in mice. *Vaccine* 31, 873-878
25. Zhao, H., Jiang, T., Zhou, X. Z., Deng, Y. Q., Li, X. F., Chen, S. P., Zhu, S. Y., Zhou, X., Qin, E. D., and Qin, C. F. (2014) Induction of neutralizing antibodies against four serotypes of dengue viruses by MixBiEDIII, a tetravalent dengue vaccine. *PloS one* 9, e86573
26. Sukupolvi-Petty, S., Austin, S. K., Purtha, W. E., Oliphant, T., Nybakken, G. E., Schlesinger, J. J., Roehrig, J. T., Gromowski, G. D., Barrett, A. D., Fremont, D. H., and Diamond, M. S. (2007) Type- and subcomplex-specific neutralizing antibodies against domain III of dengue virus type 2 envelope protein recognize adjacent epitopes. *Journal of virology* 81, 12816-12826
27. Midgley, C. M., Flanagan, A., Tran, H. B., Dejnirattisai, W., Chawansuntati, K., Jumnainsong, A., Wongwiwat, W., Duangchinda, T., Mongkolsapaya, J., Grimes, J. M., and Screaton, G. R. (2012) Structural analysis of a dengue cross-reactive antibody complexed with envelope domain III reveals the molecular basis of cross-reactivity. *Journal of immunology* (Baltimore, Md.: 1950) 188, 4971-4979
28. Valdes, I., Hermida, L., Martin, J., Menendez, T., Gil, L., Lazo, L., Castro, J., Niebla, O., Lopez, C., Bernardo, L., Sanchez, J., Romero, Y., Martinez, R., Guzman, M. G., and Guillen, G. (2009) Immunological evaluation in non-human primates of formulations based on the chimeric protein P64k-domain III of dengue 2 and two components of *Neisseria meningitidis*. *Vaccine* 27, 995-1001
29. de Alwis, R., Smith, S. A., Olivarez, N. P., Messer, W. B., Huynh, J. P., Wahala, W. M., White, L. J., Diamond, M. S., Baric, R. S., Crowe, J. E., Jr., and de Silva, A. M. (2012) Identification of human neutralizing antibodies that bind to complex epitopes on dengue virions. *Proceedings of the National Academy of Sciences of the United States of America* 109, 7439-7444
30. Smith, S. A., de Alwis, A. R., Kose, N., Harris, E., Ibarra, K. D., Kahle, K. M., Pfaff, J. M., Xiang, X., Doranz, B. J., de Silva, A. M., Austin, S. K., Sukupolvi-Petty, S., Diamond, M. S., and Crowe, J. E., Jr. (2013) The potent and broadly neutralizing human dengue virus-specific monoclonal antibody 1C19 reveals a unique cross-reactive epitope on the bc loop of domain II of the envelope protein. *mBio* 4, e00873-00813
31. Manoff, S. B., George, S. L., Bett, A. J., Yelmene, M. L., Dhanasekaran, G., Eggemeyer, L., Sausser, M. L., Dubey, S. A., Casimiro, D. R., Clements, D. E., Martyak, T., Pai, V., Parks, D. E., and Coller, B. A. (2015) Preclinical and clinical development of a dengue recombinant subunit vaccine. *Vaccine* 33, 7126-7134
32. Chen, G., Koellhoffer, J. F., Zak, S. E., Frei, J. C., Liu, N., Long, H., Ye, W., Nagar, K., Pan, G., Chandran, K., Dye, J. M., Sidhu, S. S., and Lai, J. R. (2014) Synthetic Antibodies with a Human Framework That Protect Mice from Lethal Sudan Ebolavirus Challenge. *ACS Chemical Biology* 9, 2263-2273

33. Koellhoffer, J. F., Chen, G., Sandesara, R. G., Bale, S., Ollmann Saphire, E., Chandran, K., Sidhu, S. S., and Lai, J. R. (2012) Two synthetic antibodies that recognize and neutralize distinct proteolytic forms of the Ebola virus envelope glycoprotein. *Chembiochem* 13, 2549-2557
34. Liu, Y., Regula, L. K., Stewart, A., and Lai, J. R. (2011) Synthetic Fab fragments that bind the HIV-1 gp41 heptad repeat regions. *Biochemical and biophysical research communications* 413, 611-615
35. Sidhu, S. S., and Fellouse, F. A. (2006) Synthetic therapeutic antibodies. *Nature chemical biology* 2, 682-688
36. Welch, B. D., Paduch, M., Leser, G. P., Bergman, Z., Kors, C. A., Paterson, R. G., Jardetzky, T. S., Kossiakoff, A. A., and Lamb, R. A. (2014) Probing the Functions of the Paramyxovirus Glycoproteins F and HN with a Panel of Synthetic Antibodies. *Journal of virology* 88, 11713-11725
37. Koide, S., and Sidhu, S. S. (2009) The importance of being tyrosine: lessons in molecular recognition from minimalist synthetic binding proteins. *ACS chemical biology* 4, 325-334
38. Wojcik, J., Hantschel, O., Grebien, F., Kaupe, I., Bennett, K. L., Barkinge, J., Jones, R. B., Koide, A., Superti-Furga, G., and Koide, S. (2010) A potent and highly specific FN3 monobody inhibitor of the Abl SH2 domain. *Nature structural & molecular biology* 17, 519-527
39. Ramaraj, T., Angel, T., Dratz, E. A., Jesaitis, A. J., and Mumey, B. (2012) Antigen-antibody interface properties: composition, residue interactions, and features of 53 non-redundant structures. *Biochimica et biophysica acta* 1824, 520-532
40. Bogan, A. A., and Thorn, K. S. (1998) Anatomy of hot spots in protein interfaces. *Journal of molecular biology* 280, 1-9
41. Stewart, A., Liu, Y., and Lai, J. R. (2012) A strategy for phage display selection of functional domain-exchanged immunoglobulin scaffolds with high affinity for glycan targets. *Journal of immunological methods* 376, 150-155

What is claimed is:

1. A Dengue virus glycoprotein subunit E DIII variant comprising variant Ser27 (SEQ ID NO:1), variant SerD1 (SEQ ID NO:2), variant Ala1 (SEQ ID NO:3), variant Ala2 (SEQ ID NO:4), variant Ala3 (SEQ ID NO:5), variant Ala5 (SEQ ID NO:6), variant Ala11 (SEQ ID NO:7), or variant Ala30 (SEQ ID NO:8).

2. The variant of claim 1 consisting of Ser27 (SEQ ID NO:1).

3. The variant of claim 1 consisting of SerD1 (SEQ ID NO:2).

4. The variant of claim 1 consisting of Ala1 (SEQ ID NO:3).

5. The variant of claim 1 consisting of Ala2 (SEQ ID NO:4).

6. The variant of claim 1 consisting of Ala3 (SEQ ID NO:5).

7. The variant of claim 1 consisting of Ala5 (SEQ ID NO:6).

8. The variant of claim 1 consisting of Ala11 (SEQ ID NO:7).

9. The variant of claim 1 consisting of Ala30 (SEQ ID NO:8).

10. The variant of claim 2, encoded by the nucleic acid set forth in SEQ ID NO:9.

11. The variant of claim 3, encoded by the nucleic acid set forth in SEQ ID NO:10.

12. The variant of claim 4, encoded by the nucleic acid set forth in SEQ ID NO:11.

13. The variant of claim 5, encoded by the nucleic acid set forth in SEQ ID NO:12.

14. The variant of claim 6, encoded by the nucleic acid set forth in SEQ ID NO:13.

15. The variant of claim 7, encoded by the nucleic acid set forth in SEQ ID NO:14.

16. The variant of claim 8, encoded by the nucleic acid set forth in SEQ ID NO:15.

17. The variant of claim 9, encoded by the nucleic acid set forth in SEQ ID NO:16.

18. A dimer or oligomer comprising any of the variants of claim 1.

19. A virion of an isolated, recombinant Dengue virus comprising a variant of claim 1.

20. A Dengue virus composition comprising a variant of claim 1.

21. The composition of claim 20 further comprising an immunological adjuvant.

* * * * *

SEQUENCE LISTING

```
<160> NUMBER OF SEQ ID NOS: 20

<210> SEQ ID NO 1
<211> LENGTH: 123
<212> TYPE: PRT
<213> ORGANISM: Artificial Sequence
<220> FEATURE:
<223> OTHER INFORMATION: Dengue Virus Protein

<400> SEQUENCE: 1

Asp Tyr Lys Asp Asp Asp Asp Lys Gly Ser Gly Met Ser Tyr Ser Met
1               5                   10                  15

Cys Thr Gly Lys Phe Lys Ile Val Lys Glu Ile Ala Ser Thr Ser His
            20                  25                  30

Gly Thr Ile Val Ile Arg Val Gln Tyr Glu Gly Asp Gly Ser Pro Cys
        35                  40                  45

Lys Ile Pro Phe Glu Ile Met Asp Leu Glu Lys Arg His Val Leu Gly
    50                  55                  60

Arg Leu Ile Thr Val Asn Pro Ile Val Thr Glu Lys Asp Ser Pro Val
65                  70                  75                  80

Asn Ile Glu Ala Glu Pro Pro Phe Gly Asp Ser Tyr Ile Ile Ile Gly
                85                  90                  95

Val Glu Ser Ser Gln Leu Ser Leu Asn Trp Phe Lys Lys Gly Ser Ser
            100                 105                 110

Ile Gly Gln His His His His His His His His
        115                 120


<210> SEQ ID NO 2
<211> LENGTH: 123
<212> TYPE: PRT
<213> ORGANISM: Artificial Sequence
<220> FEATURE:
<223> OTHER INFORMATION: Dengue Virus Protein

<400> SEQUENCE: 2

Asp Tyr Lys Asp Asp Asp Asp Lys Gly Ser Gly Met Ser Tyr Ser Met
1               5                   10                  15

Cys Thr Gly Lys Phe Lys Ile Val Lys Glu Ile Ala Glu Ser Ser Ser
            20                  25                  30
```

Gly Thr Ile Val Ile Arg Val Gln Tyr Glu Gly Tyr Gly Ser Pro Cys
35 40 45

Lys Ile Pro Phe Glu Ile Met Asp Leu Glu Lys Arg His Val Leu Gly
50 55 60

Arg Leu Ile Thr Val Asn Pro Ile Val Thr Glu Lys Asp Ser Pro Val
65 70 75 80

Asn Ile Glu Ala Glu Pro Pro Phe Gly Asp Ser Tyr Ile Ile Ile Gly
85 90 95

Val Glu Ser Ala Gln Leu Lys Leu Asn Trp Phe Lys Lys Gly Ser Ser
100 105 110

Ile Gly Gln His His His His His His His His
115 120

<210> SEQ ID NO 3
<211> LENGTH: 123
<212> TYPE: PRT
<213> ORGANISM: Artificial Sequence
<220> FEATURE:
<223> OTHER INFORMATION: Dengue Virus Protein

<400> SEQUENCE: 3

Asp Tyr Lys Asp Asp Asp Asp Lys Gly Ser Gly Met Ser Tyr Ser Met
1 5 10 15

Cys Thr Gly Lys Phe Lys Ile Val Lys Glu Ile Ala Ala Ala Ala Ala
20 25 30

Gly Thr Ile Val Ile Arg Val Gln Tyr Glu Gly Asp Gly Ser Pro Cys
35 40 45

Lys Ile Pro Phe Glu Ile Met Asp Leu Glu Lys Arg His Val Leu Gly
50 55 60

Arg Leu Ile Thr Val Asn Pro Ile Val Thr Glu Lys Asp Ser Pro Val
65 70 75 80

Asn Ile Glu Ala Glu Pro Pro Phe Gly Asp Ser Tyr Ile Ile Ile Gly
85 90 95

Val Ala Pro Gly Gln Leu Glu Leu Asn Trp Phe Lys Lys Gly Ser Ser
100 105 110

Ile Gly Gln His His His His His His His His
115 120

<210> SEQ ID NO 4
<211> LENGTH: 123
<212> TYPE: PRT
<213> ORGANISM: Artificial Sequence
<220> FEATURE:
<223> OTHER INFORMATION: Dengue Virus Protein

<400> SEQUENCE: 4

Asp Tyr Lys Asp Asp Asp Asp Lys Gly Ser Gly Met Ser Tyr Ser Met
1 5 10 15

Cys Thr Gly Lys Phe Lys Ile Val Lys Glu Ile Ala Ala Ala Ala Asp
20 25 30

Ala Thr Ile Val Ile Arg Val Gln Tyr Glu Gly Asp Gly Ser Pro Cys
35 40 45

Glu Ile Pro Phe Glu Ile Met Asp Leu Glu Lys Arg His Val Leu Gly
50 55 60

Arg Leu Ile Thr Val Asn Pro Ile Val Thr Glu Lys Asp Ser Pro Val
65 70 75 80

Asn Ile Glu Ala Glu Pro Pro Phe Gly Asp Ser Tyr Ile Ile Ile Gly

```
                85                  90                  95

Val Glu Ala Ala Glu Leu Lys Leu Asn Trp Phe Lys Lys Gly Ser Ser
            100                 105                 110

Ile Gly Gln His His His His His His His His
        115                 120


<210> SEQ ID NO 5
<211> LENGTH: 123
<212> TYPE: PRT
<213> ORGANISM: Artificial Sequence
<220> FEATURE:
<223> OTHER INFORMATION: Dengue Virus Protein

<400> SEQUENCE: 5

Asp Tyr Lys Asp Asp Asp Asp Lys Gly Ser Gly Met Ser Tyr Ser Met
1               5                   10                  15

Cys Thr Gly Lys Phe Lys Ile Val Lys Glu Ile Ala Ala Ala Gln Ala
            20                  25                  30

Gly Thr Ile Val Ile Arg Val Gln Tyr Glu Gly Asp Gly Ser Pro Cys
        35                  40                  45

Lys Ile Pro Phe Glu Ile Met Asp Leu Glu Lys Arg His Val Leu Gly
    50                  55                  60

Arg Leu Ile Thr Val Asn Pro Ile Val Thr Glu Lys Asp Ser Pro Val
65                  70                  75                  80

Asn Ile Glu Ala Glu Pro Pro Phe Gly Asp Ser Tyr Ile Ile Ile Gly
                85                  90                  95

Ala Ala Ala Gly Ala Leu Glu Leu Asn Trp Phe Lys Lys Gly Ser Ser
            100                 105                 110

Ile Gly Gln His His His His His His His His
        115                 120


<210> SEQ ID NO 6
<211> LENGTH: 123
<212> TYPE: PRT
<213> ORGANISM: Artificial Sequence
<220> FEATURE:
<223> OTHER INFORMATION: Dengue Virus Protein

<400> SEQUENCE: 6

Asp Tyr Lys Asp Asp Asp Asp Lys Gly Ser Gly Met Ser Tyr Ser Met
1               5                   10                  15

Cys Thr Gly Lys Phe Lys Ile Val Lys Glu Ile Ala Ala Thr Ala Asp
            20                  25                  30

Ala Thr Ile Val Ile Arg Val Gln Tyr Glu Gly Asp Gly Ser Pro Cys
        35                  40                  45

Lys Ile Pro Phe Glu Ile Met Asp Leu Glu Lys Arg His Val Leu Gly
    50                  55                  60

Arg Leu Ile Thr Val Asn Pro Ile Val Thr Glu Lys Asp Ser Pro Val
65                  70                  75                  80

Asn Ile Glu Ala Glu Pro Pro Phe Gly Asp Ser Tyr Ile Ile Ile Gly
                85                  90                  95

Ala Glu Ala Ala Pro Leu Thr Leu Asn Trp Phe Lys Lys Gly Ser Ser
            100                 105                 110

Ile Gly Gln His His His His His His His His
        115                 120


<210> SEQ ID NO 7
<211> LENGTH: 123
```

<212> TYPE: PRT
<213> ORGANISM: Artificial Sequence
<220> FEATURE:
<223> OTHER INFORMATION: Dengue Virus Protein

<400> SEQUENCE: 7

```
Asp Tyr Lys Asp Asp Asp Asp Lys Gly Ser Gly Met Ser Tyr Ser Met
1               5                   10                  15

Cys Thr Gly Lys Phe Lys Ile Val Lys Glu Ile Ala Glu Ala Ala Pro
            20                  25                  30

Gly Thr Ile Val Ile Arg Val Gln Tyr Glu Gly Asp Gly Ser Pro Cys
        35                  40                  45

Lys Ile Pro Phe Glu Ile Met Asp Leu Glu Lys Arg His Val Leu Gly
    50                  55                  60

Arg Leu Ile Thr Val Asn Pro Ile Val Thr Glu Lys Asp Ser Pro Val
65                  70                  75                  80

Asn Ile Glu Ala Glu Pro Pro Phe Gly Asp Ser Tyr Ile Ile Ile Gly
                85                  90                  95

Ala Glu Pro Gly Glu Leu Thr Leu Asn Trp Phe Lys Lys Gly Ser Ser
            100                 105                 110

Ile Gly Gln His His His His His His His His
        115                 120
```

<210> SEQ ID NO 8
<211> LENGTH: 123
<212> TYPE: PRT
<213> ORGANISM: Artificial Sequence
<220> FEATURE:
<223> OTHER INFORMATION: Dengue Virus Protein

<400> SEQUENCE: 8

```
Asp Tyr Lys Asp Asp Asp Asp Lys Gly Ser Gly Met Ser Tyr Ser Met
1               5                   10                  15

Cys Thr Gly Lys Phe Lys Ile Val Lys Glu Ile Ala Glu Thr Gln Asp
            20                  25                  30

Gly Thr Ile Val Ile Arg Val Gln Tyr Glu Gly Asp Gly Ser Pro Cys
        35                  40                  45

Lys Ile Pro Phe Glu Ile Met Asp Leu Glu Lys Arg His Val Leu Gly
    50                  55                  60

Arg Leu Ile Thr Val Asn Pro Ile Val Thr Glu Lys Asp Ser Pro Val
65                  70                  75                  80

Asn Ile Glu Ala Glu Pro Pro Phe Gly Asp Ser Tyr Ile Ile Ile Gly
                85                  90                  95

Ala Glu Pro Ala Ala Leu Glu Leu Asn Trp Phe Lys Lys Gly Ser Ser
            100                 105                 110

Ile Gly Gln His His His His His His His His
        115                 120
```

<210> SEQ ID NO 9
<211> LENGTH: 372
<212> TYPE: DNA
<213> ORGANISM: Homo sapiens

<400> SEQUENCE: 9

```
gactacaagg atgatgacga caaaggcagc ggcatgagct atagcatgtg caccggcaaa      60

tttaaaatcg tgaaagagat cgcctcgacg tcgcacggta ccattgtgat ccgtgtgcag     120

tatgaaggcg atggtagccc gtgcaaaatc ccgttcgaga tcatggacct ggagaaacgc     180
```

-continued

```
catgtgctgg gtcgcctgat taccgtgaac ccgattgtga ccgagaaaga tagcccggtg    240

aacattgaag ccgaaccgcc gttcggcgat agctacatta tcattggtgt tgagtctagt    300

cagctgagcc tgaactggtt caagaagggc agcagcattg gccagcatca tcatcatcat    360

catcatcatt aa                                                        372
```

<210> SEQ ID NO 10
<211> LENGTH: 372
<212> TYPE: DNA
<213> ORGANISM: Homo sapiens

<400> SEQUENCE: 10

```
gactacaagg atgatgacga caaaggcagc ggcatgagct atagcatgtg caccggcaaa     60

tttaaaatcg tgaaagagat cgccgagtcg tcgagcggta ccattgtgat ccgtgtgcag    120

tatgaaggct acggtagccc gtgcaaaatc ccgttcgaga tcatggacct ggagaaacgc    180

catgtgctgg gtcgcctgat taccgtgaac ccgattgtga ccgagaaaga tagcccggtg    240

aacattgaag ccgaaccgcc gttcggcgat agctacatta tcattggtgt tgagtctgct    300

cagctgaaac tgaactggtt caagaagggc agcagcattg gccagcatca tcatcatcat    360

catcatcatt aa                                                        372
```

<210> SEQ ID NO 11
<211> LENGTH: 372
<212> TYPE: DNA
<213> ORGANISM: Homo sapiens

<400> SEQUENCE: 11

```
gactacaagg atgatgacga caaaggcagc ggcatgagct atagcatgtg caccggcaaa     60

tttaaaatcg tgaaagagat cgccgcagct gcagctggta ccattgtgat ccgtgtgcag    120

tatgaaggcg atggtagccc gtgcaaaatc ccgttcgaga tcatggacct ggagaaacgc    180

catgtgctgg gtcgcctgat taccgtgaac ccgattgtga ccgagaaaga tagcccggtg    240

aacattgaag ccgaaccgcc gttcggcgat agctacatta tcattggtgt tgcaccaggt    300

caactggaac tgaactggtt caagaagggc agcagcattg gccagcatca tcatcatcat    360

catcatcatt aa                                                        372
```

<210> SEQ ID NO 12
<211> LENGTH: 372
<212> TYPE: DNA
<213> ORGANISM: Homo sapiens

<400> SEQUENCE: 12

```
gactacaagg atgatgacga caaaggcagc ggcatgagct atagcatgtg caccggcaaa     60

tttaaaatcg tgaaagagat cgccgcagct gcagatgcta ccattgtgat ccgtgtgcag    120

tatgaaggcg atggtagccc gtgcgaaatc ccgttcgaga tcatggacct ggagaaacgc    180

catgtgctgg gtcgcctgat taccgtgaac ccgattgtga ccgagaaaga tagcccggtg    240

aacattgaag ccgaaccgcc gttcggcgat agctacatta tcattggtgt tgaagcagct    300

gaactgaaac tgaactggtt caagaagggc agcagcattg gccagcatca tcatcatcat    360

catcatcatt aa                                                        372
```

<210> SEQ ID NO 13
<211> LENGTH: 372
<212> TYPE: DNA
<213> ORGANISM: Homo sapiens

<400> SEQUENCE: 13
gactacaagg atgatgacga caaaggcagc ggcatgagct atagcatgtg caccggcaaa 60
tttaaaatcg tgaaagagat cgccgcagct caagctggta ccattgtgat ccgtgtgcag 120
tatgaaggcg atggtagccc gtgcaaaatc ccgttcgaga tcatggacct ggagaaacgc 180
catgtgctgg gtcgcctgat taccgtgaac ccgattgtga ccgagaaaga tagcccggtg 240
aacattgaag ccgaaccgcc gttcggcgat agctacatta tcattggtgc tgcagcaggt 300
gcactggaac tgaactggtt caagaagggc agcagcattg gccagcatca tcatcatcat 360
catcatcatt aa 372

<210> SEQ ID NO 14
<211> LENGTH: 372
<212> TYPE: DNA
<213> ORGANISM: Homo sapiens

<400> SEQUENCE: 14
gactacaagg atgatgacga caaaggcagc ggcatgagct atagcatgtg caccggcaaa 60
tttaaaatcg tgaaagagat cgccgcaact gcagatgcta ccattgtgat ccgtgtgcag 120
tatgaaggcg atggtagccc gtgcaaaatc ccgttcgaga tcatggacct ggagaaacgc 180
catgtgctgg gtcgcctgat taccgtgaac ccgattgtga ccgagaaaga tagcccggtg 240
aacattgaag ccgaaccgcc gttcggcgat agctacatta tcattggtgc tgaagcagct 300
ccactgacac tgaactggtt caagaagggc agcagcattg gccagcatca tcatcatcat 360
catcatcatt aa 372

<210> SEQ ID NO 15
<211> LENGTH: 372
<212> TYPE: DNA
<213> ORGANISM: Homo sapiens

<400> SEQUENCE: 15
gactacaagg atgatgacga caaaggcagc ggcatgagct atagcatgtg caccggcaaa 60
tttaaaatcg tgaaagagat cgccgaagct gcacctggta ccattgtgat ccgtgtgcag 120
tatgaaggcg atggtagccc gtgcaaaatc ccgttcgaga tcatggacct ggagaaacgc 180
catgtgctgg gtcgcctgat taccgtgaac ccgattgtga ccgagaaaga tagcccggtg 240
aacattgaag ccgaaccgcc gttcggcgat agctacatta tcattggtgc tgaaccaggt 300
gaactgacac tgaactggtt caagaagggc agcagcattg gccagcatca tcatcatcat 360
catcatcatt aa 372

<210> SEQ ID NO 16
<211> LENGTH: 372
<212> TYPE: DNA
<213> ORGANISM: Homo sapiens

<400> SEQUENCE: 16
gactacaagg atgatgacga caaaggcagc ggcatgagct atagcatgtg caccggcaaa 60
tttaaaatcg tgaaagagat cgccgaaact caagatggta ccattgtgat ccgtgtgcag 120
tatgaaggcg atggtagccc gtgcaaaatc ccgttcgaga tcatggacct ggagaaacgc 180
catgtgctgg gtcgcctgat taccgtgaac ccgattgtga ccgagaaaga tagcccggtg 240
aacattgaag ccgaaccgcc gttcggcgat agctacatta tcattggtgc tgaaccagct 300

-continued

```
gcactggaac tgaactggtt caagaagggc agcagcattg gccagcatca tcatcatcat    360

catcatcatt aa                                                        372


<210> SEQ ID NO 17
<211> LENGTH: 105
<212> TYPE: PRT
<213> ORGANISM: Artificial Sequence
<220> FEATURE:
<223> OTHER INFORMATION: Dengue Virus Protein

<400> SEQUENCE: 17

Gly Met Ser Tyr Val Met Cys Thr Gly Ser Phe Lys Leu Glu Lys Glu
1               5                   10                  15

Val Ala Glu Thr Gln His Gly Thr Val Leu Val Gln Val Lys Tyr Glu
            20                  25                  30

Gly Thr Asp Ala Pro Cys Lys Ile Pro Phe Ser Thr Gln Asp Glu Lys
        35                  40                  45

Gly Val Thr Gln Asn Gly Arg Leu Ile Thr Ala Asn Pro Ile Val Thr
    50                  55                  60

Asp Lys Glu Lys Pro Val Asn Ile Glu Thr Glu Pro Pro Phe Gly Glu
65                  70                  75                  80

Ser Tyr Ile Ile Val Gly Ala Gly Glu Lys Ala Leu Lys Leu Ser Trp
                85                  90                  95

Phe Lys Lys Gly Ser Ser Ile Gly Lys
            100                 105


<210> SEQ ID NO 18
<211> LENGTH: 105
<212> TYPE: PRT
<213> ORGANISM: Artificial Sequence
<220> FEATURE:
<223> OTHER INFORMATION: Dengue Virus Protein

<400> SEQUENCE: 18

Gly Met Ser Tyr Ser Met Cys Thr Gly Lys Phe Lys Ile Val Lys Glu
1               5                   10                  15

Ile Ala Glu Thr Gln His Gly Thr Ile Val Ile Arg Val Gln Tyr Glu
            20                  25                  30

Gly Asp Gly Ser Pro Cys Lys Ile Pro Phe Glu Ile Met Asp Leu Glu
        35                  40                  45

Lys Arg His Val Leu Gly Arg Leu Ile Thr Val Asn Pro Ile Val Thr
    50                  55                  60

Glu Lys Asp Ser Pro Val Asn Ile Glu Ala Glu Pro Pro Phe Gly Asp
65                  70                  75                  80

Ser Tyr Ile Ile Ile Gly Val Glu Pro Gly Gln Leu Lys Leu Asn Trp
                85                  90                  95

Phe Lys Lys Gly Ser Ser Ile Gly Gln
            100                 105


<210> SEQ ID NO 19
<211> LENGTH: 105
<212> TYPE: PRT
<213> ORGANISM: Artificial Sequence
<220> FEATURE:
<223> OTHER INFORMATION: Dengue Virus Protein

<400> SEQUENCE: 19

Gly Met Ser Tyr Ala Met Cys Leu Asn Thr Phe Val Leu Lys Lys Glu
1               5                   10                  15
```

-continued

```
Val Ser Glu Thr Gln His Gly Thr Ile Leu Ile Lys Val Glu Tyr Lys
            20                  25                  30

Gly Glu Asp Ala Pro Cys Lys Ile Pro Phe Ser Thr Glu Asp Gly Gln
        35                  40                  45

Gly Lys Ala His Asn Gly Arg Leu Ile Thr Ala Asn Pro Val Val Thr
    50                  55                  60

Lys Lys Glu Glu Pro Val Asn Ile Glu Ala Glu Pro Pro Phe Gly Glu
65                  70                  75                  80

Ser Asn Ile Val Ile Gly Ile Gly Asp Lys Ala Leu Lys Ile Asn Trp
                85                  90                  95

Tyr Lys Lys Gly Ser Ser Ile Gly Lys
            100                 105


<210> SEQ ID NO 20
<211> LENGTH: 105
<212> TYPE: PRT
<213> ORGANISM: Artificial Sequence
<220> FEATURE:
<223> OTHER INFORMATION: Dengue Virus Protein

<400> SEQUENCE: 20

Gly Met Ser Tyr Thr Met Cys Ser Gly Lys Phe Ser Ile Asp Lys Glu
1               5                   10                  15

Met Ala Glu Thr Gln His Gly Thr Thr Val Val Lys Val Lys Tyr Glu
            20                  25                  30

Gly Ala Gly Ala Pro Cys Lys Val Pro Ile Glu Ile Arg Asp Val Asn
        35                  40                  45

Lys Glu Lys Val Val Gly Arg Ile Ile Ser Ser Thr Pro Phe Ala Glu
    50                  55                  60

Asn Thr Asn Ser Val Thr Asn Ile Glu Leu Glu Pro Pro Phe Gly Asp
65                  70                  75                  80

Ser Tyr Ile Val Ile Gly Val Gly Asp Ser Ala Leu Thr Leu His Trp
                85                  90                  95

Phe Arg Lys Gly Ser Ser Ile Gly Lys
            100                 105
```